United States Patent [19]

O'Halloran

[11] Patent Number: 6,042,574
[45] Date of Patent: Mar. 28, 2000

[54] OVAL VENTILATION EAR TUBE

[76] Inventor: Gerard O'Halloran, 3141 Dean Ct. #803, Minneapolis, Minn. 55331

[21] Appl. No.: 09/038,382

[22] Filed: Mar. 11, 1998

[51] Int. Cl.[7] .................................................. A61M 31/00
[52] U.S. Cl. ........................... 604/285; 604/93; 604/514; 623/12; 128/864
[58] Field of Search .................................... 604/264, 285, 604/174, 49, 50, 275, 93; D24/173, 155; 623/10, 11, 12, 66; 128/868, 867; D23/266

[56] References Cited

U.S. PATENT DOCUMENTS

| D. 239,330 | 3/1976 | Shea et al. . | |
|---|---|---|---|
| D. 274,753 | 7/1984 | Armstrong . | |
| D. 371,606 | 7/1996 | Doyle | D24/173 |
| 2,830,587 | 4/1958 | Everett . | |
| 4,174,716 | 11/1979 | Treace | 128/350 R |
| 4,326,512 | 4/1982 | Peerless . | |
| 4,468,218 | 8/1984 | Armstrong . | |
| 4,676,796 | 6/1987 | Merwin et al. . | |
| 4,695,275 | 9/1987 | Bruce et al. | 604/264 |
| 4,764,168 | 8/1988 | Suh | 604/264 |
| 4,775,370 | 10/1988 | Berry . | |
| 5,047,053 | 9/1991 | Jahn | 623/10 |
| 5,246,455 | 9/1993 | Shikani . | |
| 5,490,845 | 2/1996 | Racz . | |

*Primary Examiner*—Ronald K. Stright, Jr.
*Assistant Examiner*—Jeremy Thissell
*Attorney, Agent, or Firm*—Kinney & Lange, P.A.

[57] ABSTRACT

An ear tube for ventilating and equalizing the pressure between a middle ear and an outer ear. The ear tube is comprised of a shaft and a tab. The shaft further includes a top and a bottom at opposite longitudinal ends of the shaft, and a lumen with a major dimension greater in length than a perpendicular minor dimension. The tab extends outward, perpendicular from the bottom of the shaft.

24 Claims, 4 Drawing Sheets

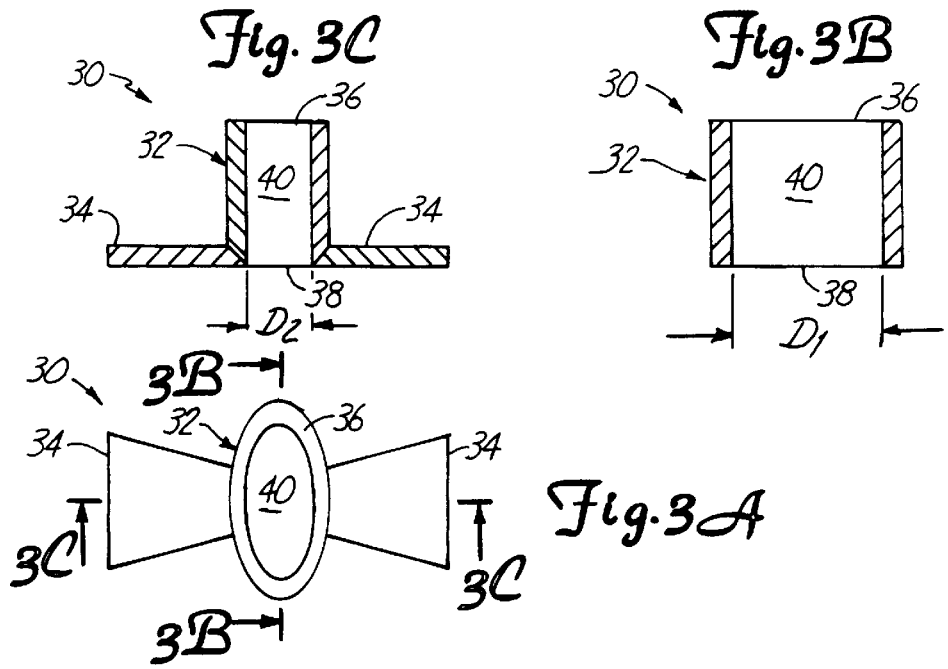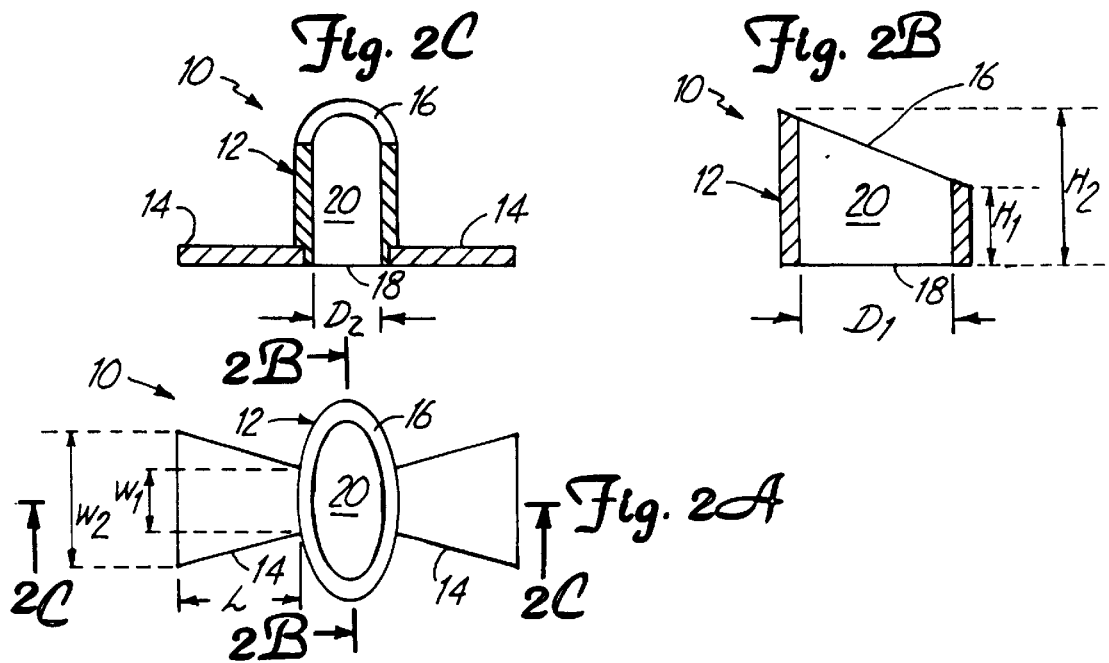

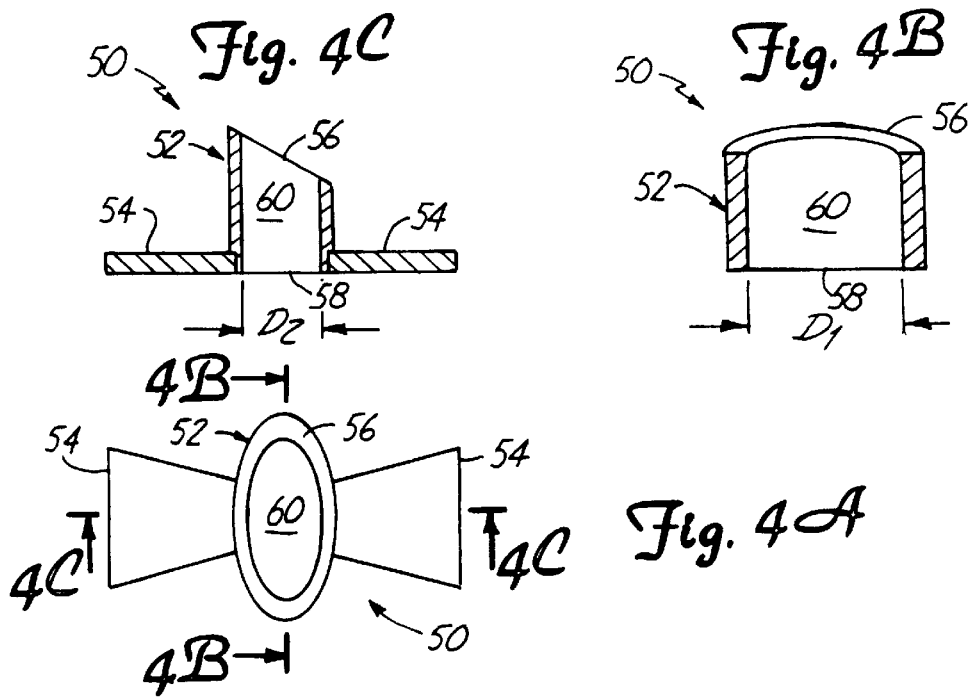
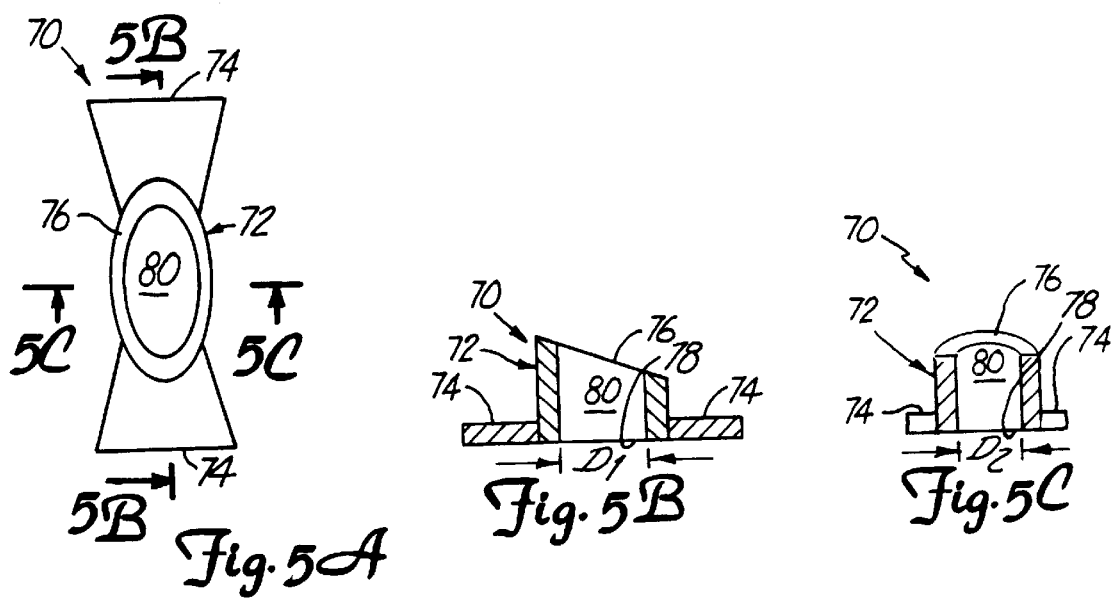

OVAL VENTILATION EAR TUBE

BACKGROUND OF THE INVENTION

The invention relates to ventilating or equalizing the pressure between the middle ear and the outer ear. More particularly, the invention relates to an oval shaped ear tube to provide improved drainage and ventilation from the middle ear to the outer ear.

Recurrent ear infections, particularly among young children, may lead to long term hearing loss or permanent retraction of the tympanic membrane or eardrum. The treatment for patients with chronic ear infections is generally to insert ventilation tubes into the tympanic membrane or eardrum to allow ventilation and drainage into the outer ear from the middle ear. By providing a ventilation or drainage path from the middle ear to the outer ear, pressure or fluid does not build up within the middle ear which can cause pain and hearing loss. Ear tubes are generally made of materials such as stainless steel, Teflon, Silastic, nylon or other similar types of materials. There is generally an inner flange on the ear tube to prevent the tube from being readily pushed out by infection or other fluid pressure building up in the middle ear region behind the ear drum. As recognized in U.S. Pat. No. 4,775,370 ('370 patent), known ear tube designs generally have a lumen of constant or uniform diameter. The '370 patent describes a technique for utilizing an ear tube that has an inner hollow circular cross section that increases along the length of the tube from the inner end to the outer end of the tube.

The current ear tube styles have several disadvantages. First, when the tubes extrude, a permanent hole or perforation may be left in the ear drum which requires surgical repair. The surgical repair is generally not performed until after an extended period of time to ensure that the child has outgrown whatever problems were causing the chronic ear infections. However, because the surgical repair may not occur for several years and water must be kept out of the ear until the perforation is repaired, the perforation may inconvenience the patient and interfere with water activities such as swimnming. The current uniform round shape of the ear tubes that are presently being used may also contribute to the formation of ear tube perforations.

Second, ear tubes often extrude too soon, or before the child has outgrown the age of ear infections. The highest incidence of ear infections generally occurs in children less than four or five years of age. Thus, tubes placed in young children less then three years of age ideally should stay in place for two or more years to allow the child to outgrow the age when ear infections are most likely to occur. Maintaining the ear tubes in place for two or more years helps avoid exposing the child to a second surgical procedure to replace the extruded ear tubes which entails the concurrent dangers of a general anesthetic. Currently, the incidence of repeat placement of ear tubes is greater than thirty percent.

Ear tubes are generally held in place by a round flange at the bottom of the tube. The round flange typically holds the tube in place for four to twelve months. Other known techniques have used a pointed flange which protrudes from the bottom of the tube. This technique typically maintains the tube in place for approximately nine to eighteen months. Another technique is to use a long, straight flange protruding from the bottom of the tube. This technique is designed to hold the tube in place permanently. Although in practice, the length of time the tube stays in place varies and averages approximately three years.

Third, ear tubes can become blocked by ear wax (cerumen) or fluid from the middle ear that has dried in the lumen of the tube. If the tube is blocked, its ability to ventilate and drain the middle ear cavity is eliminated. Most ear tubes have a relatively small round shaped lumen that is easily blocked. A blocked ear tube becomes a problem when the next ear infection occurs and the pressure builds up in the middle ear behind the eardrum. The pressure may not only wash out the puss developing in the ear, but it can also dislodge the plugged tube itself and perforate the ear drum causing extreme pain and requiring surgical repair. If surgical repair is required, then the patient will again be exposed to a general anesthetic with its own concurrent dangers.

A fourth problem with current ear tube designs is that it is difficult to examine the lumen of the tube when the tubes are in place. The difficulty in viewing the lumen is caused by the angle of the ear drum relative to the ear canal. Due to the angle of the ear drum, once the ear tube is in place it is difficult to examine the lumen and identify whether the tube is blocked by ear wax (cerumen) or dried fluid. Identifying the ear tube's source of blockage aids in determining the appropriate treatment to unblock the ear tube and ensure proper ventilation from the middle ear to the outer ear.

There is no known ear tube device which allows easy examination while implanted in the eardrum that significantly reduces the risks of extruding to soon, perforating the tympanic membrane, or blocking the ventilation path.

BRIEF SUMMARY OF THE INVENTION

The invention is a device and method for ventilating and equalizing the pressure between a middle ear and an outer ear. The invention comprises an ear tube having a shaft creating a lumen with an oval shaped cross section and a tab. The shaft is further defined by a top and a bottom that are located at opposite longitudinal ends of the shaft. The oval shaped cross section of the lumen is defined by a major dimension having a greater length than a minor dimension. The tab extends outward substantially perpendicular from the bottom of the shaft. The ear tube is implanted through an incision created in a tympanic membrane. The ear tube is implanted so that the major dimension lies substantially parallel to the incision.

BRIEF DESCRIPTION OF THE DRAWINGS

FIG. 2A is a top view of the first embodiment of the invention.

FIG. 2B is a cross sectional view along section 2B—2B of FIG. 2A.

FIG. 2C is a cross sectional view along section 2C—2C of FIG. 2A.

FIG. 3A is a top view of a second embodiment of the invention.

FIG. 3B is a cross sectional view along section 3B—3B of FIG. 3A.

FIG. 3C is a cross sectional view along section 3C—3C of FIG. 3A.

FIG. 4A is a top view of a third embodiment of the invention.

FIG. 4B is a cross sectional view along section 4B—4B of FIG. 4A.

FIG. 4C is a cross sectional view along section 4C—4C of FIG. 4A.

FIG. 5A is a top view of a fourth embodiment of the invention.

FIG. 5B is a cross sectional view along section 5B—5B of FIG. 5A.

FIG. 5C is a cross sectional view along section 5C—5C of FIG. 5A.

DETAILED DESCRIPTION OF THE PREFERRED EMBODIMENTS

Figure 1:
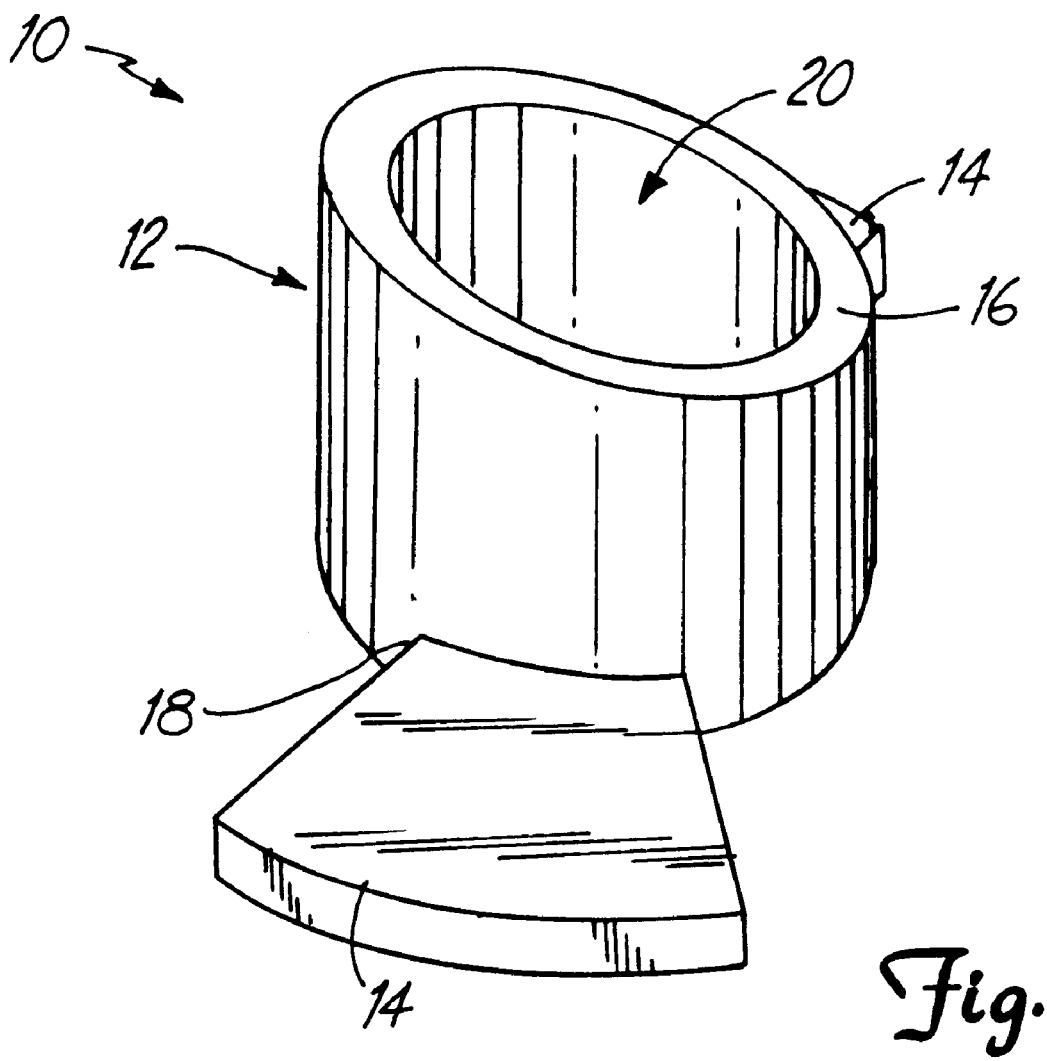
FIG. 1 is a perspective view of a first embodiment of the invention.

A first embodiment of an oval ventilation ear tube 10 is shown in FIG. 1. The ear tube 10 is comprised of an open ended shaft 12 and a pair of tabs 14. The shaft 12 has a top 16, a bottom 18 and a lumen 20. The tabs 14 extend substantially perpendicular from the bottom 18 of the shaft 12. Once the shaft 12 is implanted in a tympanic membrane, the lumen 20 provides ventilation and drainage from the middle ear to the outer ear.

In FIGS. 2A–2C, the first embodiment of the ear tube 10 is shown in a top view and cross sectional side views to more clearly illustrate the invention. FIG. 2A is a top view of the first embodiment of the invention. The generally oval shape of the lumen 20 is created by a major dimension which is greater than a minor dimension. For ease of reference, the major dimension will be referred to as a major diameter $D_1$, and the minor dimension will be referred to as a minor diameter $D_2$. Use of this reference is not intended in anyway to limit the shape of the lumen 20 to elliptical shapes. Rather, all shapes having a major dimension, or major diameter $D_1$, greater than a minor dimension, or diameter minor $D_2$, are within the scope of the claimed invention. Such generalized shapes include but are not limited to ovals, ellipses, diamonds, ovoids, or rectangles. While reference may be made to, and the figures depict, a generally oval shaped lumen 20 for the ear tube 12, the various other shapes identified above and which satisfy the general requirements of the major dimension being greater than the minor dimension are also considered to be within the scope of the invention.

As shown in FIGS. 2B–2C, the major diameter $D_1$ is greater than the minor diameter $D_2$. In a preferred embodiment, the major diameter $D_1$ is perpendicular to the minor diameter $D_2$. With the major diameter $D_1$ larger than the minor diameter $D_2$, the ear tube 10 is more likely to extrude without perforating or leaving a permanent hole in the tympanic membrane. It may also improve drainage from the middle ear to the outer ear decreasing the likelihood of the ear tube 10 becoming blocked.

In a preferred embodiment, the tabs 14 extend from the shaft 12 in opposite directions. The tabs 14 assist in retaining the ear tube 10 in the tympanic membrane for a desired period of time. To this aim, the width of the tabs 14 increase as the tabs 14 extend from the shaft 12. As shown in FIG. 2A, the tabs 14 preferably have a trapezoidal shape with a width $W_1$ (where the tabs 14 extend from the shaft 12) being less than a width $W_2$ (at an outer end of the tabs 14 which is farthest from the shaft 12). Additionally, the length L that the tabs 14 extend from the shaft 12 can be adjusted to alter the period of time the ear tubes 10 remain implanted. The greater the length L that the tabs 14 extend from the shaft 12, then the longer they will remain implanted. By varying the length L that the tabs 14 extend from the shaft 12, the ear tube 10 can be customized on a case by case basis to match the period of time the patient is most likely to experience chronic ear infections. The shape of the tabs 14 also reduces the risk of premature extrusion and the likelihood that a second surgical procedure is necessary. This helps avoid repeat exposure to the concurrent dangers of a general anesthetic as a result of a second surgical procedure. Instead, the ear tube 10 remains implanted until the likelihood of future ear infections has reduced to the point that the ear tube 10 is no longer necessary and then extrudes without perforating the tympanic membrane.

Shown in FIGS. 2B and 2C are cross sectional side views of the ear tube 10 along sections 2B—2B and 2C—2C, respectively. The top 16 of the first embodiment of the ear tube 10 is beveled. Specifically, the top 16 is beveled in a direction defined by the major diameter $D_1$ such that a height $H_1$ of the shaft 12 is shorter at one end of the major diameter $D_1$ than a height $H_2$ of the shaft 12 at the opposite end of the major diameter $D_1$. The bevel improves the ability to examine the ear tube 10 once implanted in the tympanic membrane to ensure that it remains unblocked. Additionally in FIGS. 2B and 2C, the tabs 14 are more clearly shown to extend perpendicular from the bottom 18 of the shaft 12.

In FIGS. 3A–3C, similar top and cross sectional side views of a second embodiment of an ear tube 30 is shown. The second embodiment 30, similar to the first embodiment 10, has a shaft 32 and a pair of tabs 34 which extend perpendicular from the shaft 32. The shaft 32 has a top 36, a bottom 38 and a lumen 40 with a generally oval shaped cross section. The oval shape of the lumen 40 is again defined by the major diameter $D_1$ which has a greater length than the perpendicular minor diameter $D_2$. Also, similar to the first embodiment of the ear tube 10, the width of the tabs 34 of the second embodiment 30 increase as the tabs 34 extend from the bottom 38 of the shaft 32 in a direction defined by the minor diameter $D_2$. However, unlike the first embodiment of the ear tube 10, the top 36 of the second embodiment of the ear tube 30 is not beveled.

In FIGS. 4A–4C, similar top and cross sectional side views show a third embodiment of an oval shaped ear tube 50. The ear tube 50 similarly includes a shaft 52 with a pair of tabs 54. The shaft 52 has a top 56, a bottom 58 and a lumen 60. The oval shape of the lumen 60 is defined by the major diameter $D_1$ which has a length that is greater than a perpendicular minor diameter $D_2$. Similar to the first and second embodiments, the tabs 54 extend perpendicular from the bottom 58 of the shaft 52 in a direction defined by the minor diameter $D_2$. Unlike the second embodiment of the ear tube 30, the top 56 of the third embodiment 50 is beveled. However, also unlike the first embodiment of the ear tube 10, the top 56 is beveled in a direction defined by the minor diameter $D_2$. Changing the position or presence of the bevel at the top 16, 36 or 56, increases the flexibility of how the ear tube 10, 30 or 50, respectively, can be implanted to ensure visability.

A fourth embodiment of an ear tube 70 is shown in FIGS. 5A–5C with similar top and cross sectional side views. Again, the ear tube 70 includes a shaft 72 and a pair of tabs 74. The shaft 72 has a top 76, a bottom 78 and a lumen 80. The lumen 80 has a generally oval shape defined by the major diameter $D_1$ which is longer than the perpendicular minor diameter $D_2$. Similar to the previous embodiments, the width of the tabs 74 are trapezoidal in shape, and increase as they extend perpendicular from the shaft 72. However, unlike the previous embodiments, the tabs 74 extend in a direction defined by the major diameter $D_1$ rather than the minor diameter $D_2$. The top 76 of the shaft 72 is also shown beveled in a direction defined by the major diameter $D_1$. However, the top 76 could also be beveled in a direction defined by the minor diameter $D_2$ as shown in FIGS. 4A–4C.

Figure 6:
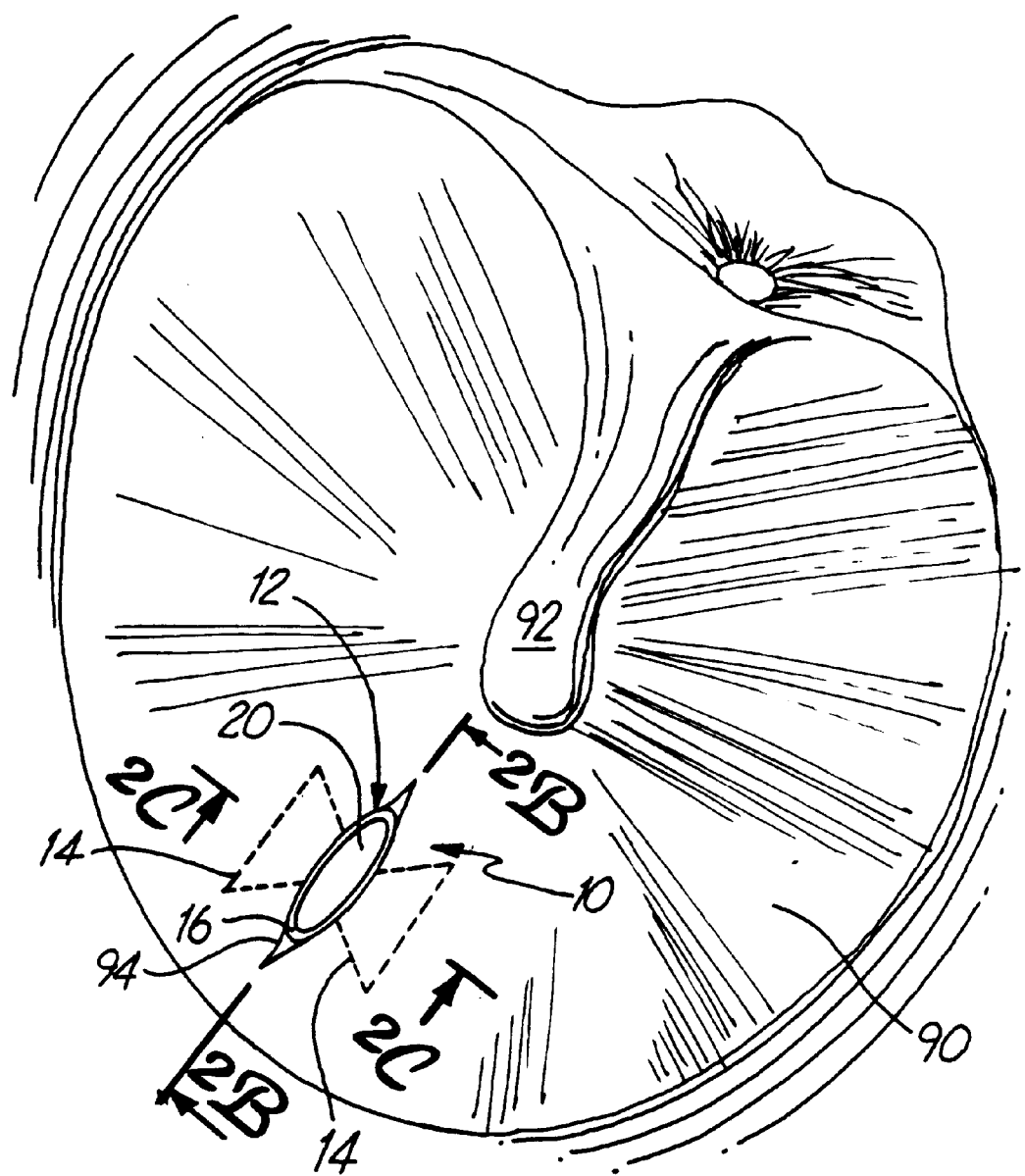
FIG. 6 is a top view of the first embodiment of the invention implanted in a tympanic membrane.

In FIG. 6, an exaggerated view of the first embodiment of the ear tube 10 is shown implanted in a tympanic membrane 90. The tympanic membrane 90, or eardrum, is part of the middle ear and creates a barrier between the middle and outer ear. A malleus 92, which is located behind the tympanic membrane 90 and is the largest of three small bones in the middle ear, is shown as a reference point.

To implant the ear tube 10, an incision 94 must be made in the tympanic membrane 90. The incision 94 can be made either radially, as shown, or circumferentially. The length of the incision 94 is slightly longer than the major diameter $D_1$. Once the incision is made, the tabs 14 and bottom 18 of the shaft 12 are inserted through the incision 94. This is accomplished by either inserting one of the tabs 14 through the incision 94 at a time, or compressing the tabs 14 together below the bottom 18 of the shaft 12 for insertion through the incision 94 at the same time. If the latter technique is used, then once the tabs 14 are inserted through the incision 94 they are released and return to their position of extending perpendicularly from the shaft 12, as shown in phantom in FIG. 6.

Once the tabs 14 and the bottom 18 of the shaft 12 are inserted through the incision 94 in the tympanic membrane 90, the shaft 12 may have to be rotated so that the major diameter $D_1$ is in line with the incision 94. Also, if the top 16 is beveled, then the shaft 12 is positioned so that the shorter side $H_1$ is closest to the center of the tympanic membrane 90 and the higher side $H_2$ is closest to the perimeter of the tympanic membrane 90. The same positioning technique, of locating the shorter side $H_1$ closest to the center of the tympanic membrane 90 and the higher side $H_2$ closest to the perimeter of the tympanic membrane 90, applies to circumferential incisions as well as other embodiments of the invention such as is shown in FIGS. 4 and 5. Positioning the bevel in this manner will facilitate examination of the ear tube 10, 50 or 70 once implanted.

Although the present invention has been described with reference to preferred embodiments, workers skilled in the art will recognize that changes may be made in form and detail without departing from the spirit and scope of the invention. For example, the length of the major and minor diameters of the lumen, or the length and width of the tabs can be adjusted. Further, while the lumen has been referred to as having a generally oval cross sectional shape, other shapes having a major dimension or diameter greater in length than a perpendicular minor dimension or diameter could also be used. These shapes include an ellipse, an ovoid, a rectangle, or a diamond among others. The direction or use of a beveled top can also be adjusted depending upon the particular needs of each patient. For example, the top can be beveled along a path between the major and minor diameters, or the degree the top is beveled can be adjusted. Thus, by use of the oval ventilation ear tube, the ear tube will be easier to examine, less likely to prematurely extrude or perforate the ear drum and will more likely remain unblocked.

What is claimed is:

1. An ear tube for ventilating and equalizing pressure between a middle ear and an outer ear, wherein the ear tube comprises:
    a shaft having a top, a bottom and a lumen, wherein the top and the bottom are located at opposite longitudinal ends of the shaft and the lumen is defined by a major dimension that is greater than a minor dimension and wherein the top is beveled in a direction defined by the minor dimension; and
    a tab extending outward from the bottom of the shaft.

2. The ear tube of claim 1, wherein a pair of tabs extend radially outward from the bottom of the shaft.

3. The ear tube of claim 2, wherein the tabs extend from opposite sides of the shaft.

4. The ear tube of claim 3, wherein the tabs extend in a direction defined by the minor dimension.

5. The ear tube of claim 3, wherein the tabs extend in a direction defined by the major dimension.

6. The ear tube of claim 1, wherein the major dimension is perpendicular to the minor dimension.

7. The ear tube of claim 1, wherein the width of the tab increases as the tab extends radially outward from the bottom of the shaft.

8. The ear tube of claim 1, wherein the ear tube is made of a semi-flexible material.

9. An ear tube for ventilating and equalizing pressure between a middle ear and an outer ear, the ear tube comprising:
    a shaft having a top, a bottom and a lumen, wherein the top and bottom are located at opposite longitudinal ends of the tube and the lumen is defined by a major dimension which is greater in length and perpendicular to a minor dimension; and
    a tab having a trapezoidal shape which extends outward perpendicular from the bottom of the shaft such that an outer end of the tab is wider than an inner end of the tab which contacts the shaft.

10. The ear tube of claim 9, wherein the top is beveled.

11. The ear tube of claim 10, wherein the top is beveled in a direction defined by the major dimension.

12. The ear tube of claim 10, wherein the top is beveled in a direction defined by the minor dimension.

13. The ear tube of claim 9, wherein the ear tube includes a pair of tabs which extend outward substantially perpendicular from the bottom of the shaft in opposite directions.

14. The ear tube of claim 13, wherein the pair of tabs extend from the bottom of the shaft in a direction defined by the major dimension.

15. The ear tube of claim 13, wherein the pair of tabs extend from the bottom of the shaft in a direction defined by the minor dimension.

16. The ear tube of claim 9, wherein the ear tube is made from semi-flexible material.

17. An ear tube for ventilating and equalizing pressure between a middle ear and an outer ear, wherein the ear tube comprises:
    a shaft having a top, a bottom and a lumen, wherein the top and the bottom are located at opposite longitudinal ends of the shaft and the lumen is defined by a major dimension that is greater than a minor dimension; and
    a tab extending outward from the bottom of the shaft having a narrower region closer to the shaft and a wider region further from the shaft.

18. The ear tube of claim 17, wherein a pair of tabs extend radially outward from the bottom of the shaft.

19. The ear tube of claim 18, wherein the tabs extend from opposite sides of the shaft.

20. The ear tube of claim 17, wherein the major dimension is perpendicular to the minor dimension.

21. The ear tube of claim 17, wherein the top of the shaft is beveled.

22. A method of ventilating and equalizing the pressure between a middle ear and an outer ear, the method comprising:
    cutting a tympanic membrane to form a slit;
    inserting at least one tab that extends from a bottom of a shaft of an ear tube through the slit, the tab having a narrower region closer to the shaft and a wider region farther from the shaft;

inserting the bottom of the shaft of the ear tube through the slit, the shaft having a lumen with a major dimension which is longer than a perpendicular minor dimension of the lumen; and rotating the shaft as necessary so that the major dimension of the lumen is substantially parallel with the slit.

23. The method of claim 22, wherein inserting at least one tab comprises:

compressing together a pair of tabs that extend from the bottom of the shaft of the ear tube;

inserting the compressed tabs through the slit in the tympanic membrane; and releasing the compressed tabs once they are inserted beyond the slit in the tympanic membrane and into the middle ear.

24. The method of claim 22, wherein inserting at least one tab comprises inserting a pair of tabs that extend from the bottom of the ear tube through the incision in the tympanic membrane one at a time.

* * * * *